(12) United States Patent
Ushida

(10) Patent No.: US 12,083,297 B2
(45) Date of Patent: Sep. 10, 2024

(54) GUIDE WIRE

(71) Applicant: ASAHI INTECC CO., LTD., Seto (JP)

(72) Inventor: Keisuke Ushida, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 890 days.

(21) Appl. No.: 17/119,402

(22) Filed: Dec. 11, 2020

(65) Prior Publication Data

US 2021/0093839 A1 Apr. 1, 2021

Related U.S. Application Data

(63) Continuation of application No. PCT/JP2018/024871, filed on Jun. 29, 2018.

(51) Int. Cl.
*A61M 25/09* (2006.01)

(52) U.S. Cl.
CPC ............ *A61M 25/09* (2013.01); *A61M 2025/09083* (2013.01); *A61M 2205/0266* (2013.01)

(58) Field of Classification Search
CPC ............... A61M 25/09–0905; A61M 2025/09008–09191
See application file for complete search history.

(56) References Cited

U.S. PATENT DOCUMENTS

| | | | |
|---|---|---|---|
| 3,452,742 | A | 7/1969 | Muller |
| 4,430,083 | A | 2/1984 | Ganz et al. |
| 6,348,041 | B1 * | 2/2002 | Klint ............... A61M 25/09 600/585 |
| 2007/0049847 | A1 | 3/2007 | Osborne |
| 2011/0245730 | A1 | 10/2011 | Satozaki |
| 2017/0291013 | A1 * | 10/2017 | Pereira ............ A61M 25/09 |

FOREIGN PATENT DOCUMENTS

| | | |
|---|---|---|
| JP | 2002-505167 A | 2/2002 |
| JP | 2002-210019 A | 7/2002 |
| JP | 2005-304891 A | 11/2005 |
| JP | 2011-206494 A | 10/2011 |
| JP | 2012205800 A | 10/2012 |
| JP | 2013-126512 A | 6/2013 |
| JP | 2013-192914 A | 9/2013 |
| JP | 2015-013005 A | 1/2015 |
| JP | 2017-196368 A | 11/2017 |
| JP | 2018-108119 A | 7/2018 |
| WO | 99/44668 A1 | 9/1999 |
| WO | 2014-203336 A1 | 12/2014 |

* cited by examiner

*Primary Examiner* — David J. McCrosky
(74) *Attorney, Agent, or Firm* — Oliff PLC

(57) ABSTRACT

A guide wire includes a core shaft and a coil body including a wire wound around the core shaft. The wire includes a long axis and a short axis in a transverse section. The coil body includes an inclined portion where an angle formed by the long axis of the wire and an axial line of the coil body is acute.

17 Claims, 19 Drawing Sheets

GUIDE WIRE

CROSS REFERENCE TO RELATED APPLICATIONS

The present application is a Bypass Continuation of PCT/JP2018/024871, filed Jun. 29, 2018, the entirety of the prior application being hereby incorporated by reference into this application.

TECHNICAL FIELD

The disclosed embodiments relate to a guide wire.

BACKGROUND ART

There is known a guide wire used for inserting a catheter into a blood vessel. A guide wire made of a metal coil generally includes a core shaft employing a wire (a wire material) and a coil body formed by winding a wire around the core shaft. For example, Patent Literature 1 discloses a feature that in such a guide wire, a hydrophilic coating is applied to a surface of a coil body to facilitate passage through a constricted blood vessel and a lesioned region. For example, Patent Literature 2 discloses an apparatus for manufacturing a coil body by using a wire having a substantially circular cross section.

CITATION LIST

Patent Literature

Patent Literature 1: Japanese Unexamined Patent Application Publication (Translation of PCT Application) No. 2002-505167
Patent Literature 2: Japanese Unexamined Patent Application Publication No. 2002-210019

SUMMARY

Problem to be Solved

Even in a complicated bifurcation region (such as a thin distal blood vessel and a blood vessel with a lesion at a bifurcation point), selectivity (vascular selectivity) is required for the guide wire so that an operator can correctly select a target blood vessel to deliver the guide wire. In this respect, the guide wire described in Patent Literature 1 has a problem that the guide wire slips on an inner wall of a blood vessel at a bifurcation region, and thus, the selectivity is not sufficient. A guide wire including the coil body manufactured by the manufacturing apparatus described in Patent Literature 2 is required to make further improvement in terms of selectivity.

The guide wire has another problem that, when the guide wire passes through a healthy region, and when the guide wire reaches and passes through a lesioned region, the guide wire does not provide sufficient discriminability for an operator to determine whether the guide wire passes through the healthy region or the lesioned region in a blood vessel. If a lesion has progressed to calcification, it is obvious that the guide wire reaches the lesioned region judging from a large resistance against the guide wire being pushed; however, in a thrombosis in an atheroma state, the degree of hardening of the thrombus is low, and thus the guide wire is further pushed forward with a relatively small resistance, as a result of which it is necessary to improve discriminability to determine whether the guide wire reaches the lesioned region.

The guide wire has a problem that, when the guide wire enters a bent region of a blood vessel, the guide wire entering the bent region falls off from the bent region as a result of a shape of the guide wire being restored due to elasticity of the guide wire itself, and therefore it is necessary to prevent the guide wire from falling off.

Such a problem is not limited to the guide wire to be inserted into a vascular system, but is common to guide wires to be inserted into various organs in a human body, such as a lymphatic system, a biliary system, a urinary system, a respiratory system, a digestive system, a secretory gland, and the reproductive organs.

The disclosed embodiments have been made to solve the above-mentioned problems, and an object thereof is to provide a guide wire with which it is possible to realize improvement of at least one of selectivity (vascular selectivity), discriminability required when passing through a lesioned region, and prevention of the guide wire from easily falling off from a bent region after the guide wire enters the bent region of a blood vessel, or the like.

The disclosed embodiments have been made to solve at least some of the above-described problems, and can be implemented as the following aspects.
(1) According to one aspect of the disclosed embodiments, a guide wire is provided. The guide wire includes a core shaft and a coil body formed by winding a wire around the core shaft, in which the wire includes a long axis and a short axis in a transverse section, and the coil body includes an inclined portion where an angle formed by the long axis of the wire and an axial line of the coil body is acute with respect to a first direction along the axial line of the coil body.

According to this configuration, the coil body includes the inclined portion where the angle formed by the long axis of the wire and the axial line of the coil body is acute with respect to the first direction along the axial line of the coil body. That is, in the inclined portion, the wire forming the coil body is wound obliquely toward the first direction. When the wire is thus wound obliquely, in the inclined portion, each corner part of the wire protrudes in a second direction opposite to the first direction. In the guide wire with this configuration, when each corner part of the wire protruding in the second direction is caught on an inner wall of a blood vessel, and the like, a frictional resistance different between when the guide wire is pushed forward and when the guide wire is pulled back is applied, and therefore, it is possible to improve the selectivity (vascular selectivity).
(2) In the guide wire according to the above aspect, the coil body may further include a flat portion in which the angle formed by the long axis of the wire and the axial line of the coil body is parallel. According to this configuration, the coil body further includes the flat portion in which the angle formed by the long axis of the wire and the axial line of the coil body is parallel. In the flat portion, the wire forming the coil body is wound flat with respect to the axial line of the coil body, so that no protrusion is formed on the surface of the coil body. Therefore, in the guide wire with this configuration, it is possible to improve the selectivity (vascular selectivity) in the inclined portion and to facilitate passage through a constricted blood vessel or a lesioned region in the flat portion.
(3) In the guide wire according to the above aspect, the inclined portion may be arranged at a distal end side of the coil body, and the flat portion may be arranged at a proximal end side of the coil body. When the guide wire is inserted into the blood vessel, a reaction force applied to the guide wire is greater from an area near a center portion to the proximal end side than at the distal end side in an axial direction. According to this configuration, if the inclined portion receiving a high frictional resistance, as compared to the flat portion, depending on an advancing direction of the guide wire is arranged at a distal end side where the reaction force applied to the guide wire is small, and the flat portion receiving a constant frictional resistance is arranged at the proximal end side where the reaction force applied to the guide wire is large, it is possible to prevent the guide wire from damaging an inner wall of a blood vessel, or the like.

(4) In the guide wire according to the above aspect, in the inclined portion, the wire may be wound such that a distance between an end point at the distal end side of the long axis and the axial line is shorter than a distance between an end point at the proximal end side of the long axis and the axial line. According to this configuration, the wire in the inclined portion is wound such that the distance between the end point at the distal end side of the long axis and the axial line of the coil body is shorter than the distance between the end point at the proximal end side of the long axis and the axial line of the coil body, and therefore, the first direction is set toward the distal end side of the coil body, and the second direction is set toward the proximal end side of the coil body. That is, the guide wire with this configuration has a configuration in which the wire in the inclined portion is wound obliquely toward the distal end side of the coil body, and each corner part of the wire protrudes toward the proximal end side of the coil body. Therefore, it is possible to provide a guide wire having a low frictional resistance when the guide wire is pushed forward and a high frictional resistance when the guide wire is pulled back as a result of each corner part of the wire in the inclined portion being caught on the inner wall of a blood vessel, or the like.

(5) In the guide wire according to the above aspect, in the inclined portion, the wire may be wound such that a distance between an end point at the distal end side of the long axis and the axial line is longer than a distance between an end point at the proximal end side of the long axis and the axial line. According to this configuration, the wire in the inclined portion is wound such that the distance between the end point at the distal end side of the long axis and the axial line of the coil body is longer than the distance between the end point at the proximal end side of the long axis and the axial line of the coil body, and therefore, the first direction is set toward the proximal end side of the coil body, and the second direction is set toward the distal end side of the coil body. That is, the guide wire with this configuration has a configuration in which the wire in the inclined portion are wound obliquely toward the proximal end side of the coil body, and each corner part of the wire protrudes toward the distal end side of the coil body. Therefore, it is possible to provide a guide wire having a high frictional resistance as a result of each corner part of the wire in the inclined portion being caught on the inner wall of a blood vessel, or the like when the guide wire is pushed forward and having a low frictional resistance when the guide wire is pulled back.

(6) In the guide wire according to the above aspect, the transverse section of the wire may be of substantially elliptical shape. According to this configuration, when the transverse section of the wire is of substantially elliptical shape, it is possible to prevent the corner parts protruding in the second direction from damaging the inner wall of the blood vessel, or the like.

It is noted that the disclosed embodiments may be implemented in various aspects including, for example, a coil body of a guide wire, a method for manufacturing a coil body, and a method for manufacturing a guide wire.

DETAILED DESCRIPTION OF EMBODIMENTS

First Embodiment

Figure 1:
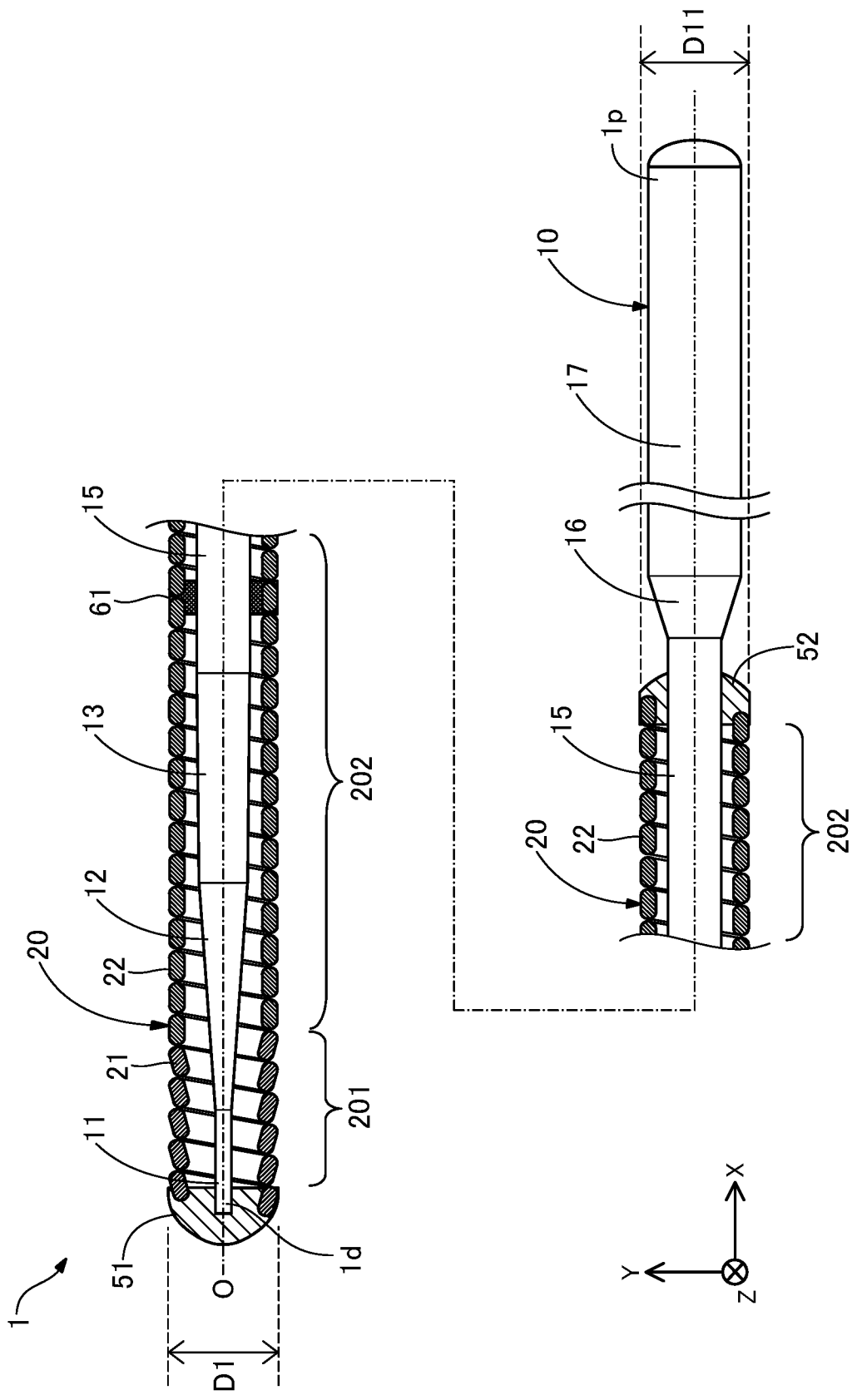
FIG. 1 is a partial sectional view illustrating an overall configuration of a guide wire according to a first embodiment.

FIG. 1 is a partial sectional view illustrating an overall configuration of a guide wire 1 according to a first embodiment. The guide wire 1 is a medical device used when a catheter is inserted into, for example, a blood vessel, and includes a core shaft 10, a coil body 20, a distal end side fixing part 51, a proximal end side fixing part 52, and an intermediate fixing part 61. In FIG. 1, an axis passing through a center of the guide wire 1 is represented by an axial line O (dot and dash line). In the following embodiments, an axis passing through a center of the core shaft 10 and an axis passing through a center of the coil body 20 both coincide with the axial line O. It is noted that the axis passing through the center of the core shaft 10 and the axis passing through the center of the coil body 20 may not coincide with the axial line O.

FIG. 1 illustrates an X-axis, a Y-axis, and a Z-axis orthogonal to one another. The X-axis corresponds to an axial direction of the guide wire 1, the Y-axis corresponds to a height direction of the guide wire 1, and the Z-axis corresponds to a width direction of the guide wire 1. A left side (−X-axis direction) in FIG. 1 is referred to as "distal end side" of the guide wire 1 and the components thereof, and a right side (+X-axis direction) in FIG. 1 is referred to as "proximal end side" of the guide wire 1 and the components. Further, with respect to the guide wire 1 and the components, an end part located at the distal end side is referred to as "distal end part" or simply "distal end," and an end part located at the proximal end side is referred to as "proximal end part" or simply "proximal end." In the present embodiment, the distal end side corresponds to "distal side," and the proximal end side corresponds to "proximal side." These features are common to the drawings illustrating the overall configurations after FIG. 1.

The core shaft 10 is a tapered long member having a large diameter at the proximal end side and a small diameter at the distal end side. The core shaft 10 may be formed of a material such as a stainless alloy including SUS304 and SUS316, a superelastic alloy including a nickel-titanium (NiTi) alloy, a piano wire, a nickel-chromium base alloy, a cobalt alloy, and tungsten. The core shaft 10 may be formed of a well-known material other than the materials listed above. The core shaft 10 includes a small-diameter part 11, a first reduced-diameter part 12, a second reduced-diameter part 13, a first large-diameter part 15, a third reduced-diameter part 16, and a second large-diameter part 17, in this order from the distal end side to the proximal end side. An outer diameter and a length of each of the parts may be arbitrarily set.

The small-diameter part 11 is placed at the distal end part of the core shaft 10. The small-diameter part 11 is a part where the outer diameter of the core shaft 10 is smallest, and has a substantially cylindrical shape having a constant outer diameter. The first reduced-diameter part 12 is placed between the small-diameter part 11 and the second reduced-diameter part 13. The first reduced-diameter part 12 reduces in the outer diameter from the proximal end side toward the distal end side to form a substantially frustoconical shape. The second reduced-diameter part 13 is placed between the first reduced-diameter part 12 and the first large-diameter part 15. The second reduced-diameter part 13 reduces in the outer diameter from the proximal end side toward the distal end side to form a substantially frustoconical shape. The first large-diameter part 15 is placed between the second reduced-diameter part 13 and the third reduced-diameter part 16. The first large-diameter part 15 has a substantially cylindrical shape having a constant outer diameter larger than the outer diameter of the small-diameter part 11. The third reduced-diameter part 16 is placed between the first large-diameter part 15 and the second large-diameter part 17. The third reduced-diameter part 16 reduces in the outer diameter from the proximal end side toward the distal end side to form a substantially frustoconical shape. The second large-diameter part 17 is placed at the proximal end part of the core shaft 10. The second large-diameter part 17 has a substantially cylindrical shape having a constant outer diameter larger than the outer diameter of the first large-diameter part 15.

Outer surfaces of the small-diameter part 11, the first reduced-diameter part 12, the second reduced-diameter part 13, and the first large-diameter part 15 are covered with the coil body 20 described below. On the other hand, the third reduced-diameter part 16 and the second large-diameter part 17 are not covered with the coil body 20 and are exposed from the coil body 20. An operator uses the second large-diameter part 17 to grip the guide wire 1.

Figure 4:
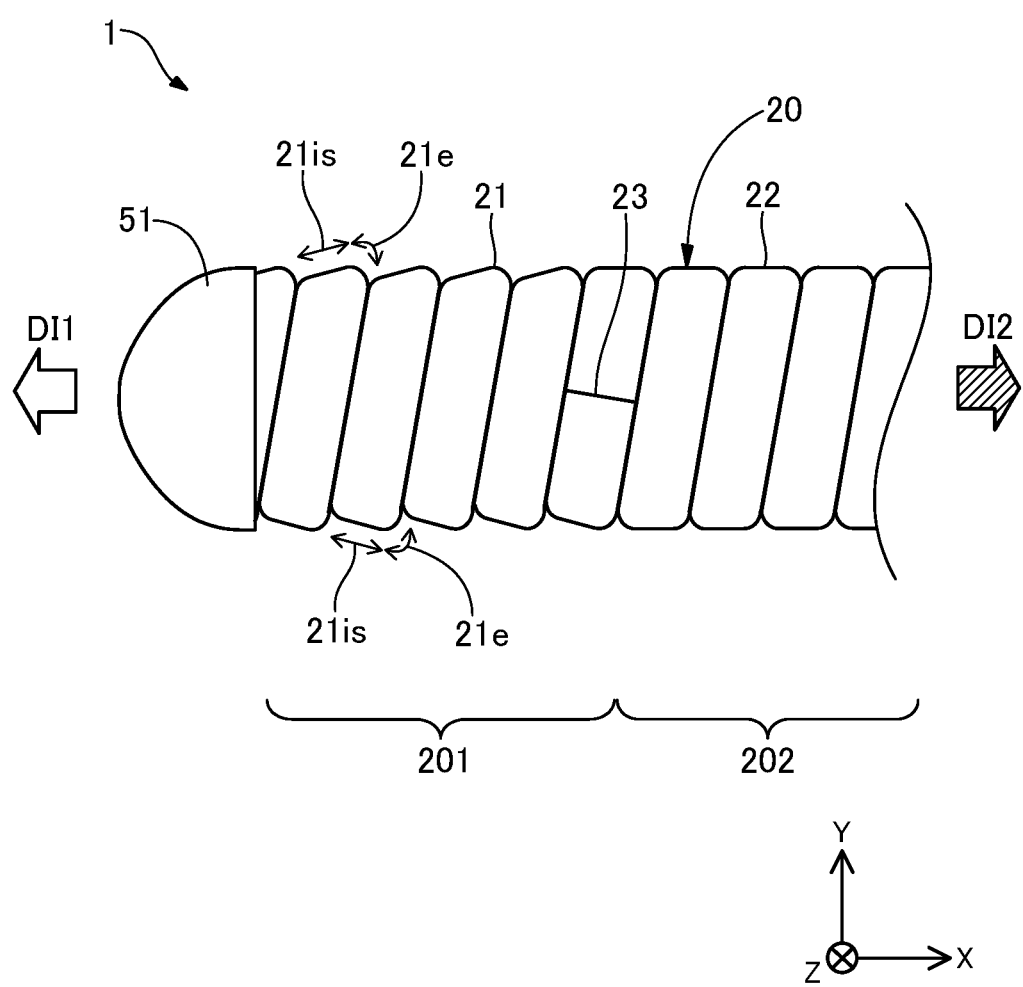
FIG. 4 is a plan view illustrating the distal end side of the guide wire in an enlarged manner.

The coil body 20 has a substantially hollow cylindrical shape formed by spirally winding a wire around the core shaft 10. The coil body 20 of the present embodiment includes an inclined portion 201 arranged at the distal end side and a flat portion 202 arranged at the proximal end side. The inclined portion 201 is formed by using a first wire 21, and the flat portion 202 is formed by using a second wire 22. The first wire 21 and the second wire 22 are joined by a not-illustrated bonding agent (FIG. 4: a joint part 23). As described above, the first wire 21 and the second wire 22 forming the coil body 20 are joined to form a single wire, and therefore, the coil body 20 is configured as a single coil. An average coil diameter in the coil body 20 (an average diameter of the outer and inner diameters of the coil body 20) may be arbitrarily determined.

Figure 2:
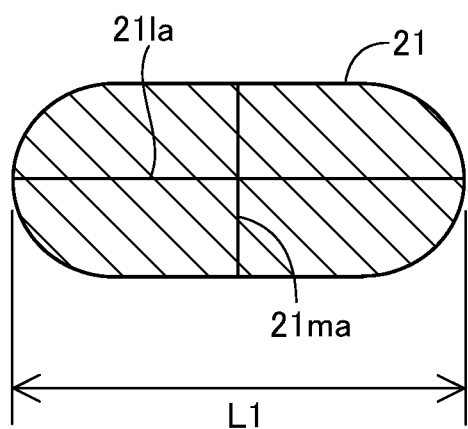
FIG. 2 is a transverse sectional view of a first wire.

FIG. 2 is a transverse sectional view of the first wire 21. As illustrated in FIG. 2, a transverse section of the first wire 21 is of substantially elliptical shape with a long axis 211*a* and a short axis 21*ma*. In the present embodiment, an ellipse (so-called super ellipse) in which a "squared" portion in the well-known ellipse equation is a power larger than the square is also included in the substantially elliptical shape. Further, in the present embodiment, with respect to any transverse section of the first wire 21, a longest portion out of a length L1 in a longitudinal direction is referred to as "long axis 211*a*", and a vertical bisector of the long axis 211*a* drawn inside the transverse section is referred to as "short axis 21*ma*". A length of the long axis 211*a* and a length of the short axis 21*ma* may be arbitrarily determined. The first wire 21 may be formed of a radiopaque alloy such as platinum or an alloy containing platinum (for example, a platinum-nickel alloy). The first wire 21 may be formed of a well-known material other than the materials listed above.

Similarly to the first wire 21 illustrated in FIG. 2, a transverse section of the second wire 22 is of substantially elliptical shape with a long axis and a short axis. A length of the long axis and a length of the short axis of the second wire 22 may be arbitrarily determined. The second wire 22 may be formed of, for example, a stainless alloy such as SUS304 and SUS316, a superelastic alloy such as a Ni—Ti alloy, a piano wire, a nickel-chromium base alloy, a radiolucent alloy such as a cobalt alloy, gold, platinum, tungsten, and a radiopaque alloy such as an alloy containing these elements (for example, a platinum-nickel alloy). The second wire 22 may be formed of a well-known material other than the materials listed above. The transverse sectional shape, the length of the long axis, the length of the short axis, and the material of the second wire 22 may be the same as or different from those of the first wire 21.

Figure 3:
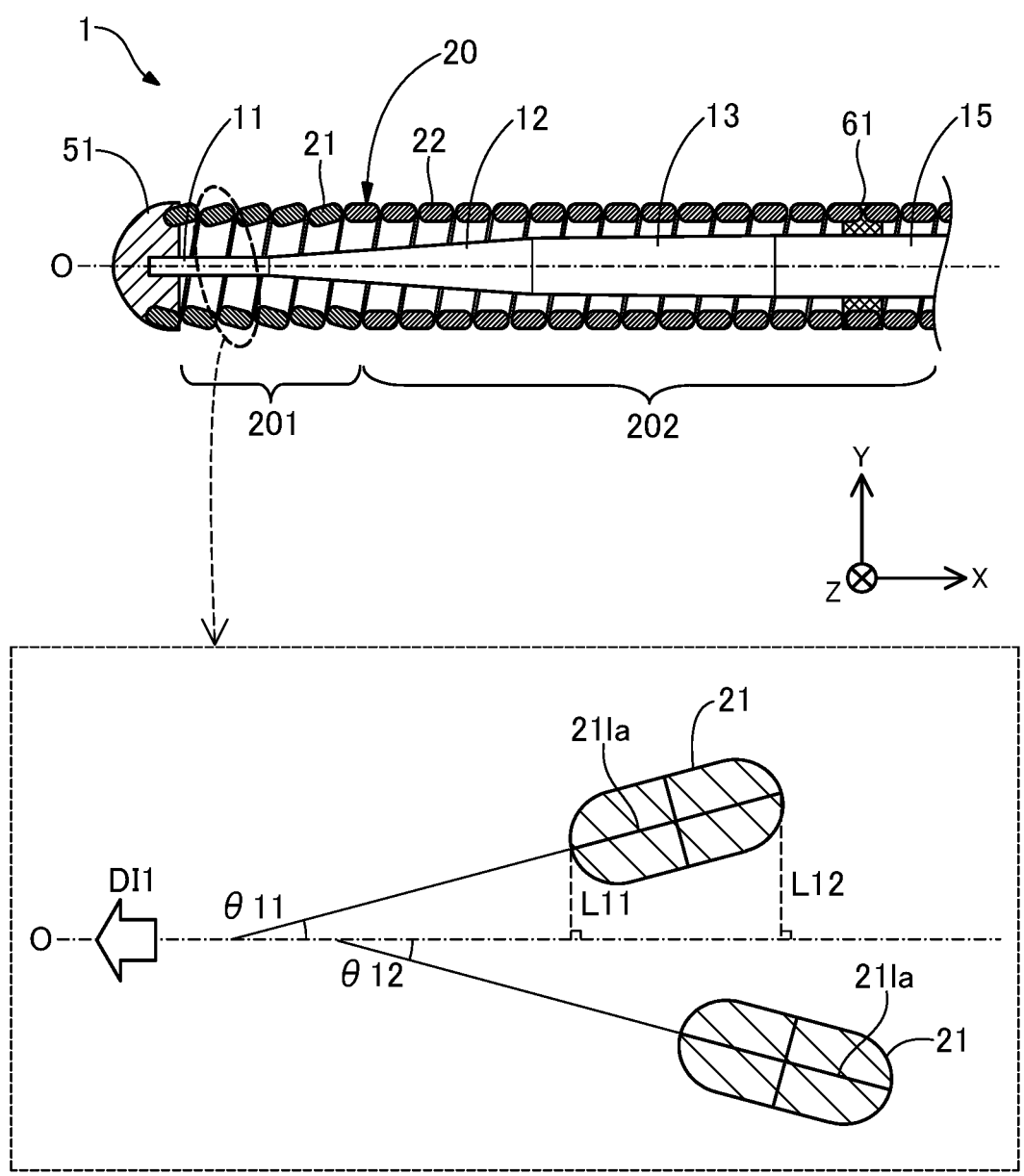
FIG. 3 is a partial sectional view of a distal end side of the guide wire.

FIG. 3 is a partial sectional view of the distal end side of the guide wire 1. In FIG. 3, a partially enlarged view of the distal end side of the guide wire 1 is illustrated in an upper part, and an enlarged view illustrating a broken line frame portion of the first wire 21 is illustrated in a lower part. As illustrated in the lower part of FIG. 3, in the first wire 21 in the inclined portion 201, both angles θ11 and θ12 formed by the long axis 211*a* and the axial line O (dot and dash line) of the coil body 20 are acute (that is, less than 90 degrees) with respect to a first direction DI1 running along the axial line O. Here, the "angle formed by the long axis and the axial line" means an angle formed by the axial line O and an extended line of the long axis 211*a* projected on a virtual plane if the long axis 211a is projected on the virtual plane including the axial line O. In the present embodiment, the first direction DI1 along the axial line O is oriented toward the distal end side of the coil body 20.

As illustrated in the lower part of FIG. 3, the first wire 21 in the inclined portion 201 is oriented so that a distance L11 between an end point at the distal end side of the long axis 211a and the axial line O of the coil body 20 is shorter than a distance L12 between an end point at the proximal end side of the long axis 211a and the axial line O of the coil body 20. Here, the "distance between the end point and the axial line" means a length of a perpendicular line drawn to the axial line O from each end point of the long axis 211a projected on a virtual plane if the long axis 211a is projected on the virtual plane including the axial line O.

On the other hand, as illustrated in the upper part of FIG. 3, in the second wire 22 in the flat portion 202, the long axis and the axial line O of the coil body 20 are parallel (i.e., the angle is zero with respect to the axial line O). As illustrated in FIG. 1, in the coil body 20 of the present embodiment, an outer diameter D1 at the distal end side and an outer diameter D11 at the proximal end side are substantially the same, but these outer diameters D1 and D11 may be different from each other.

Returning to FIG. 1 to continue the description, the distal end side fixing part 51 is placed at the distal end part of the guide wire 1, and integrally holds the distal end part of the core shaft 10 (distal end part of the small-diameter part 11) and the distal end part of the coil body 20 (distal end part of the inclined portion 201). The distal end side fixing part 51 can be formed by any bonding agent, for example, silver solder, gold solder, and metal solder of zinc, Sn—Ag alloy, Au—Sn alloy, or the like or an adhesive such as an epoxy adhesive. The proximal end side fixing part 52 is placed at the proximal end part of the first large-diameter part 15 of the core shaft 10, and integrally holds the core shaft 10 and the proximal end part of the coil body 20 (proximal end part of the flat portion 202). The proximal end side fixing part 52 can be formed by any bonding agent, similarly to the distal end side fixing part 51. The same bonding agent or different bonding agents may be used for the proximal end side fixing part 52 and the distal end side fixing part 51.

The intermediate fixing part 61 integrally holds the coil body 20 (flat portion 202) and the core shaft 10 at or near an intermediate portion of the coil body 20 in an axial line O direction. The intermediate fixing part 61 can be formed by any bonding agent, similarly to the distal end side fixing part 51. A bonding agent used for the intermediate fixing part 61 and a bonding agent used for the distal end side fixing part 51 may be the same or different from each other. In FIG. 1, only one intermediate fixing part 61 is illustrated, but the guide wire 1 may include a plurality of the intermediate fixing parts 61.

FIG. 4 is a plan view illustrating the distal end side of the guide wire 1 in an enlarged manner. As illustrated in FIG. 4, in the inclined portion 201, the first wire 21 forming the coil body 20 is wound obliquely toward the distal end side (first direction DI1) of the coil body 20. Thus, when the first wire 21 is wound obliquely, each of surfaces of the first wire 21 (that is, a surface of the coil body 20) is formed with a slope 21is inclined to be extended from the distal end side (first direction DI1) toward the proximal end side (second direction DI2) and a corner part 21e protruding toward the proximal end side (second direction DI2). It is noted that the "second direction DI2" is a direction opposite to the first direction DI1.

Figure 5:
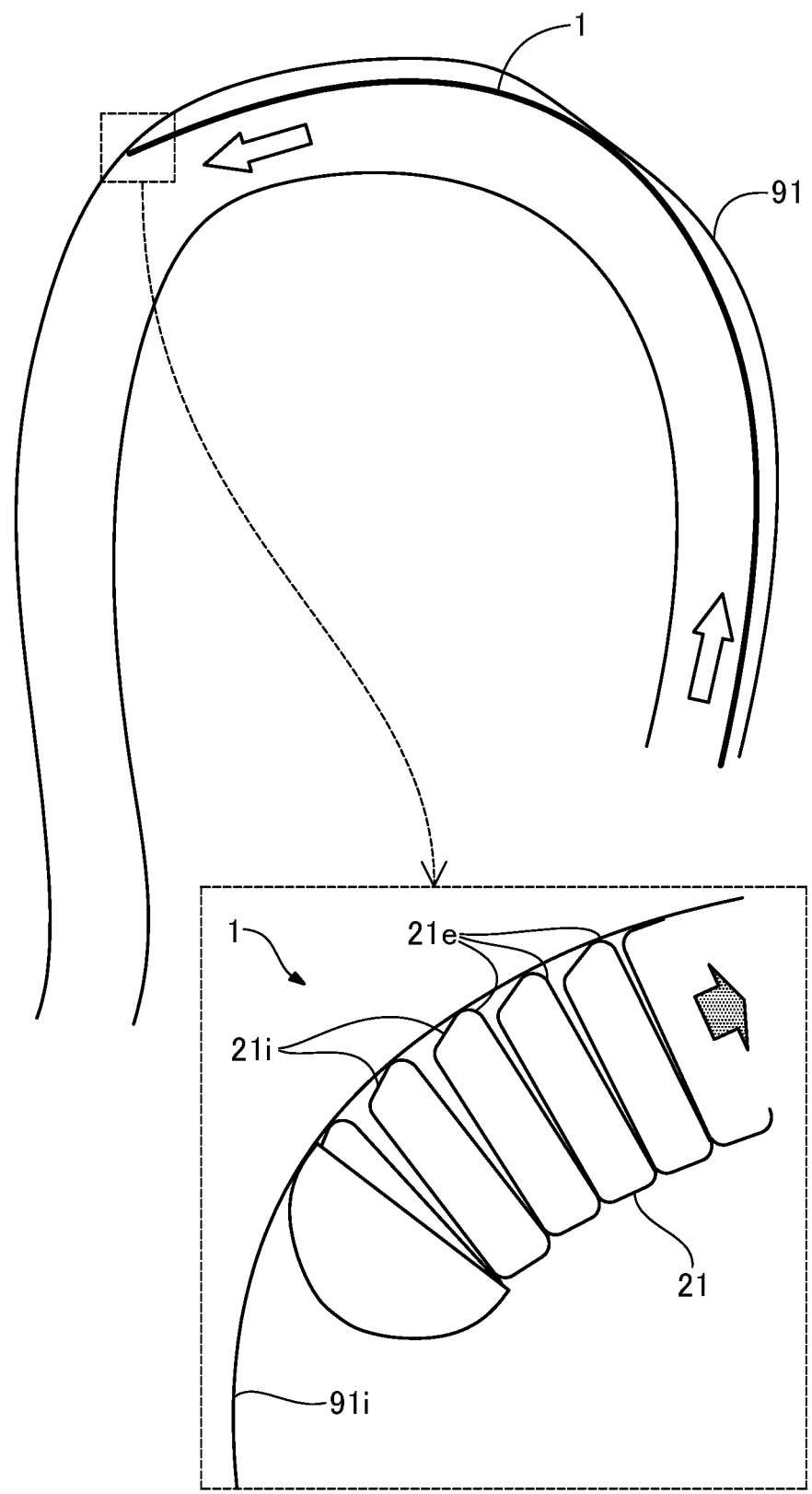
FIG. 5 is a diagram illustrating an example of when the guide wire is used.

FIG. 5 is a diagram illustrating an example of when the guide wire 1 is used. In FIG. 5, the guide wire 1 inserted into a blood vessel 91 is illustrated in an upper part, and an enlarged view of the distal end side of the guide wire 1 (an enlarged view illustrating a broken line frame portion) is illustrated in a lower part. As described above, in the guide wire 1 according to the present embodiment, the inclined portion 201 includes the slope 21is inclined from the distal end side (first direction DI1) of the coil body 20 toward the proximal end side (second direction DI2). Therefore, it is possible to reduce a frictional resistance applied to the guide wire 1 when the guide wire 1 is pushed into the blood vessel 91 as compared to a configuration without the inclined portion 201, and it is therefore easy to push the guide wire 1 into the blood vessel 91 (the upper part of FIG. 5: a white arrow indicates the direction when the guide wire 1 is pushed into the blood vessel 91).

Here, a case where a force is applied in a direction from which the guide wire 1 is pulled from the blood vessel 91, as a result of the guide wire 1 being pushed into the curved (bent) blood vessel 91, for example, due to a difference in rigidity between a distal portion and a proximal portion of the curved guide wire 1, and a case where a force is applied in a direction from which the guide wire 1 is pulled from the blood vessel 91, as a result of the distal end part of the guide wire 1 abutting against an inner wall 91i of the blood vessel 91, are considered (the lower part of FIG. 5: a hatched arrow indicates the direction when the guide wire 1 is stretched). Even in such a case, in the guide wire 1 according to the present embodiment, in the inclined portion 201, the corner part 21e protruding toward the proximal end side (second direction DI2) of the coil body 20 is caught on the inner wall 91i of the blood vessel 91, and thus, it is possible to increase the frictional resistance applied to the guide wire 1 as compared to a configuration without the inclined portion 201. As a result, the guide wire 1 according to the present embodiment can prevent a case where, after the guide wire 1 enters a curved region (bent portion) during use, the guide wire 1 falls out of the curved region (bent portion).

As described above, in the guide wire 1 according to the present embodiment, when the corner part 21e of the first wire 21 protruding toward the proximal end side (second direction DI2) of the coil body 20 is caught on the inner wall 91i of the blood vessel 91 and the like, frictional resistances different between when the guide wire 1 is pushed forward (the upper part of FIG. 5: the white arrow) and when the guide wire 1 is pulled back (the lower part of FIG. 5: the hatched arrow) are applied, and therefore, it is possible to improve the selectivity (vascular selectivity).

In the guide wire 1 according to the present embodiment, the coil body 20 includes the flat portion 202 in which the long axis of the second wire 22 and the axial line O of the coil body 20 are parallel to each other. In the flat portion 202, the second wire 22 forming the coil body 20 is wound to be flat with respect to the axial line O of the coil body 20, so that no protrusion is formed on the surface of the coil body 20 (FIG. 4). Thus, in the guide wire 1 according to the present embodiment, it is possible to facilitate the passage through a lesioned region or a constricted blood vessel in the flat portion 202.

When the guide wire 1 is inserted into the blood vessel 91, a reaction force applied to the guide wire 1 is greater from an area near a center portion to the proximal end side than at the distal end side in the axial line O direction. According to the guide wire 1 of the present embodiment, the inclined portion 201 in which the frictional resistance is increased depending on an advancing direction of the guide wire 1 as compared to the flat portion 202, is arranged at the distal end side in which the reaction force applied to the guide wire 1 is small. On the other hand, the flat portion 202 having a constant frictional resistance is arranged at the proximal end side in which the reaction force applied to the guide wire 1 is large. Therefore, in the guide wire 1 according to the present embodiment, it is possible to prevent the guide wire 1 from damaging the inner wall 91i of the blood vessel 91 or the like.

In the guide wire 1 according to the present embodiment, when the transverse sections of the first wire 21 and the second wire 22 forming the coil body 20 are of substantially elliptical shape, it is possible to prevent the corner part 21e of the first wire 21 protruding toward the proximal end side (second direction DI2) of the coil body 20 from damaging the inner wall 91i of the blood vessel 91 and the like.

In the guide wire 1 according to the present embodiment, there is a difference in resistance between when the guide wire 1 is pushed forward and when the guide wire 1 is pulled back while the guide wire 1 passes through the lesioned region, and therefore, it is possible to improve the discriminability to determine whether the guide wire 1 passes through a healthy region or passes through the lesioned region.

Second Embodiment

Figure 6:
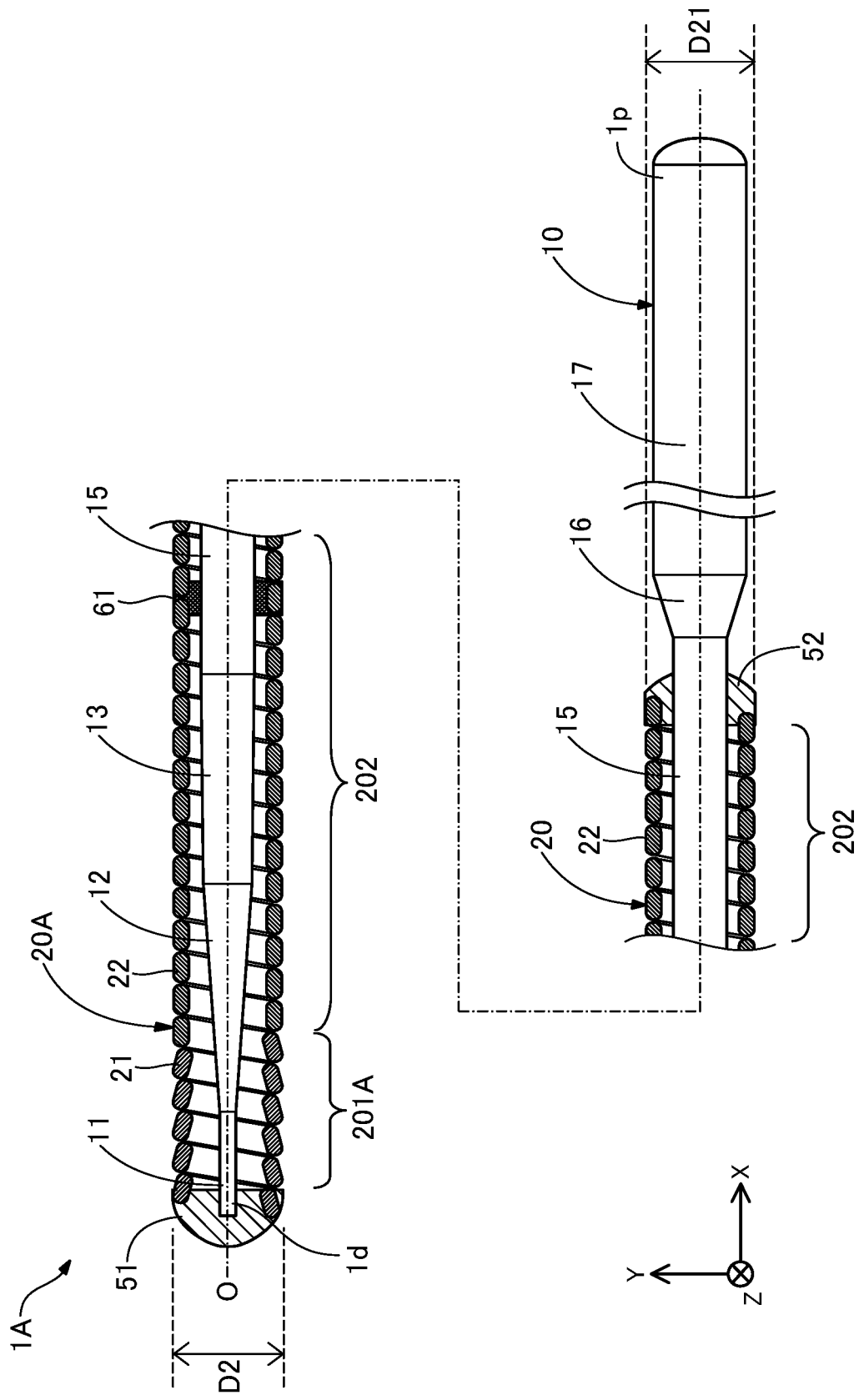
FIG. 6 is a partial sectional view illustrating an overall configuration of a guide wire according to a second embodiment.
Figure 7:
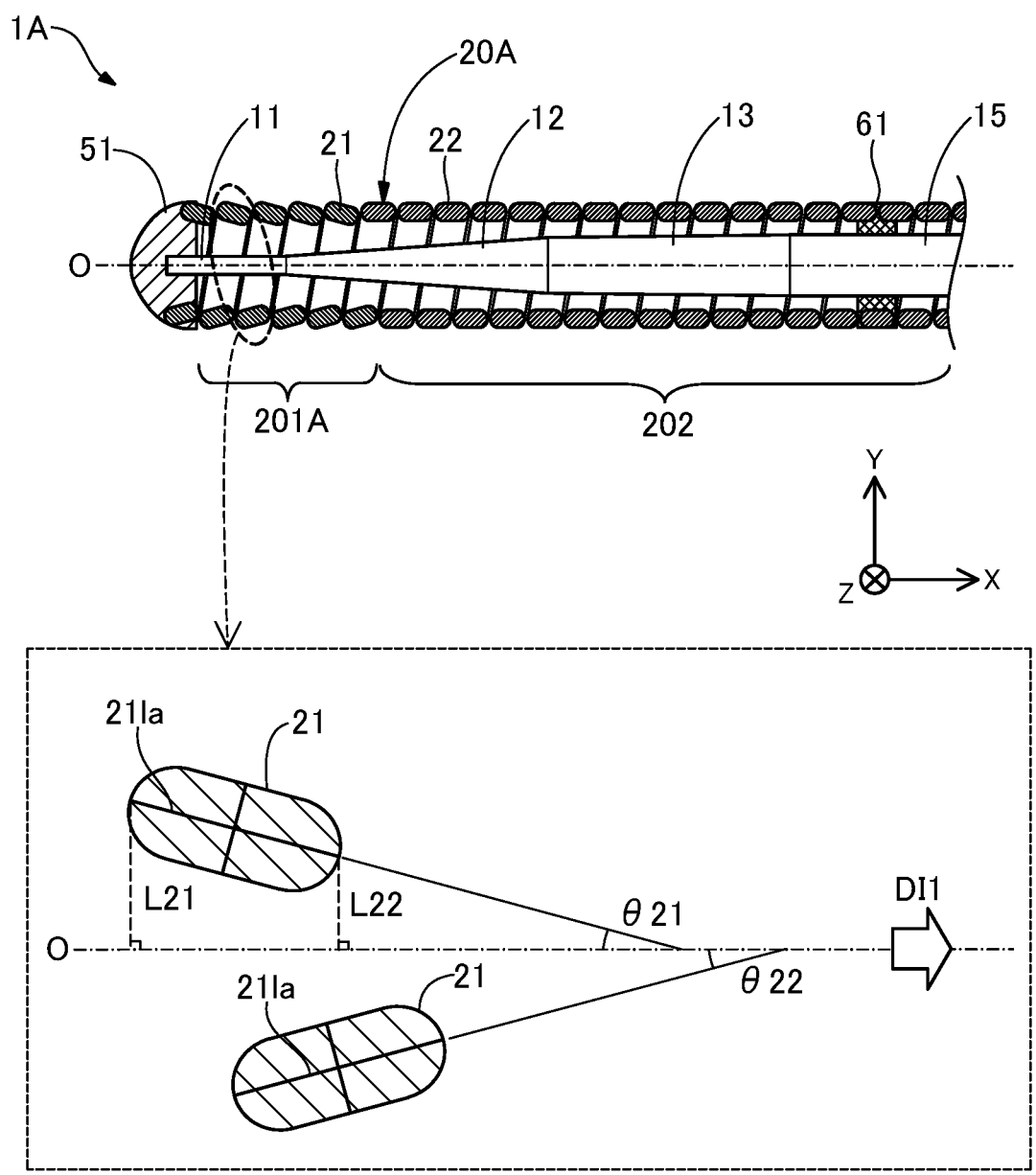
FIG. 7 is a partial sectional view of a distal end side of the guide wire according to the second embodiment.

FIG. 6 is a partial sectional view illustrating an overall configuration of a guide wire 1A according to a second embodiment. FIG. 7 is a partial sectional view of a distal end side of the guide wire 1A according to the second embodiment. An upper part and a lower part of FIG. 7 are similar in configuration to those of FIG. 3. The guide wire 1A according to the second embodiment includes an inclined portion 201A in which, in a coil body 20A, the first wire 21 is wound in a direction opposite to that of the first embodiment.

As illustrated in the lower part of FIG. 7, in the first wire 21 in the inclined portion 201A, both angles θ21 and θ22 formed by the long axis 211a and the axial line O (dot and dash line) of the coil body 20A are acute (that is, less than 90 degrees) with respect to the first direction DI1 running along the axial line O. Here, in the second embodiment, the first direction DI1 is set to be opposite to that in the first embodiment, that is, set to a direction toward the proximal end side of the coil body 20A. The first wire 21 in the inclined portion 201A is oriented so that a distance L21 between an end point at the distal end side of the long axis 211a and the axial line O of the coil body 20A is longer than a distance L22 between an end point at the proximal end side of the long axis 211a and the axial line O of the coil body 20A.

Figure 8:
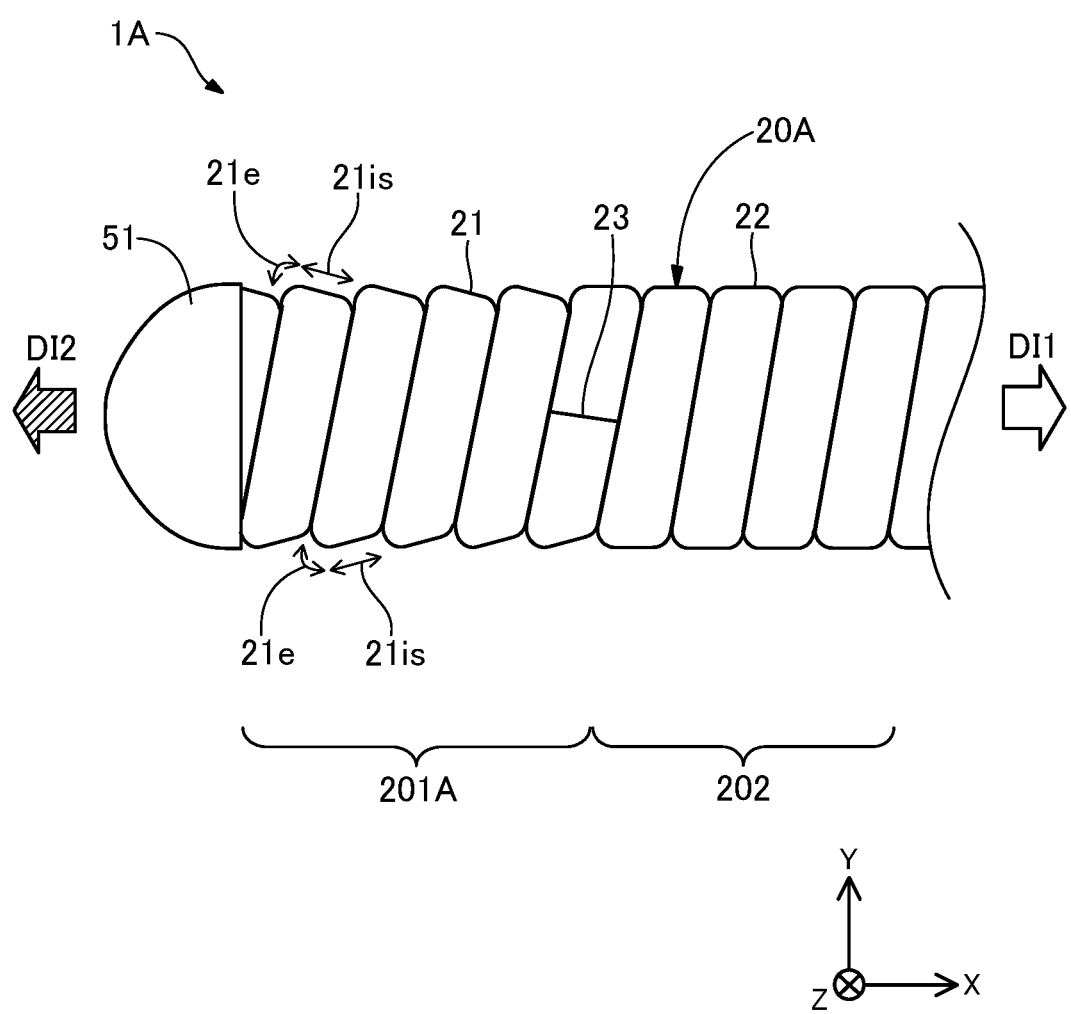
FIG. 8 is a plan view illustrating the distal end side of the guide wire according to the second embodiment in an enlarged manner.

FIG. 8 is a plan view illustrating the distal end side of the guide wire 1A according to the second embodiment in an enlarged manner. As illustrated in FIG. 8, in the inclined portion 201A, the first wire 21 forming the coil body 20A is wound obliquely toward the proximal end side (first direction DI1) of the coil body 20A. Thus, when the first wire 21 is wound obliquely, each of the surfaces of the first wire 21 (that is, a surface of the coil body 20A) is formed with the slope 21is inclined to be extended in the direction opposite to that in the first embodiment, that is, from the proximal end side (first direction DI1) toward the distal end side (second direction DI2) and the corner part 21e protruding toward the direction opposite to that in the first embodiment, that is, toward the distal end side (second direction DI2).

Figure 9:
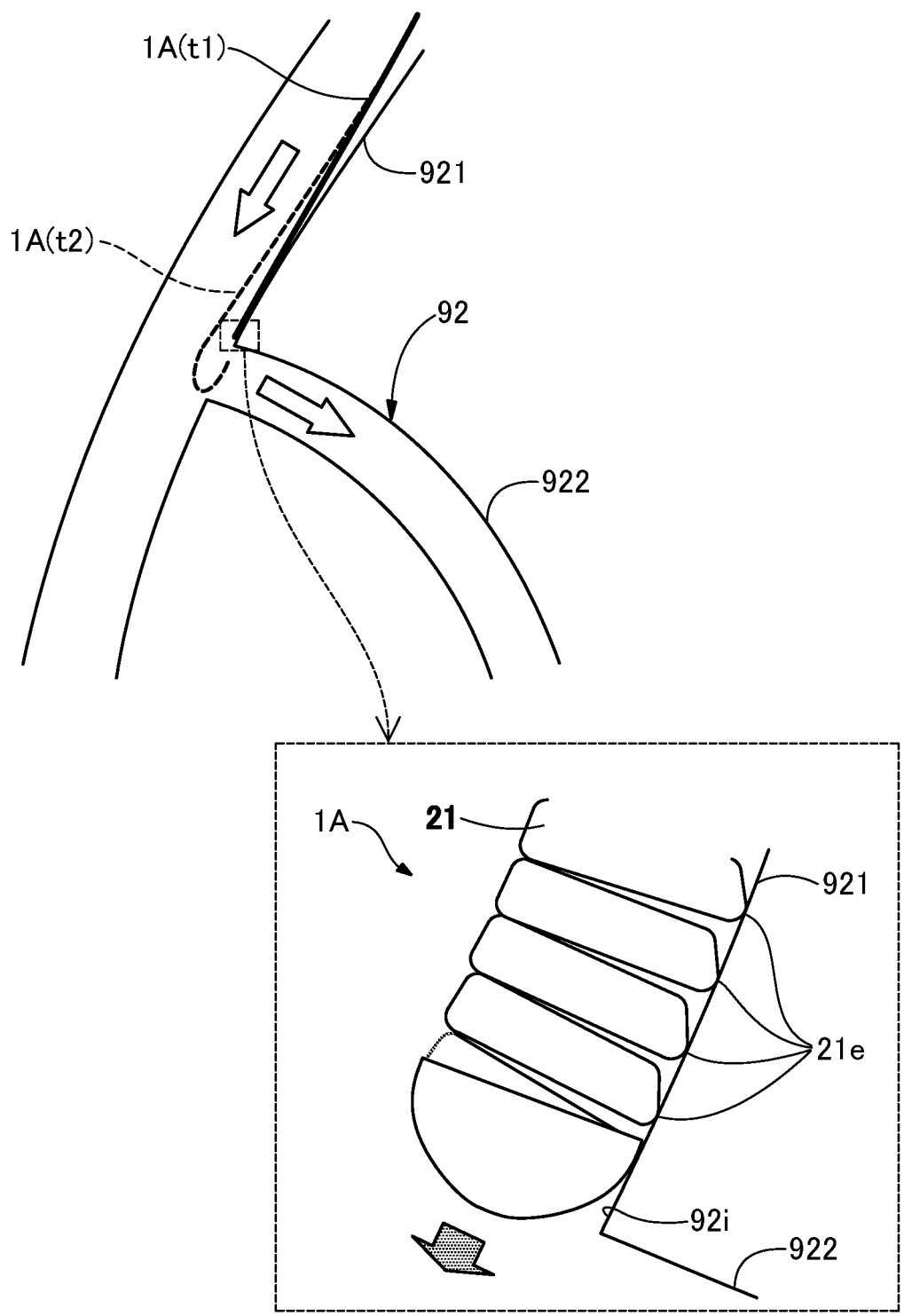
FIG. 9 is a diagram illustrating an example of when the guide wire according to the second embodiment is used.

FIG. 9 is a diagram illustrating an example of when the guide wire 1A according to the second embodiment is used. An upper part and a lower part of FIG. 9 are similar in configuration to those of FIG. 5. In the guide wire 1A according to the second embodiment, in the inclined portion 201A, the slope 21is inclined to be extended from the proximal end side (first direction DI1) of the coil body 20A toward the distal end side (second direction DI2) is formed. Therefore, when the guide wire 1A with the distal end side not being curved is pushed into a proximal blood vessel 921 (the upper part of FIG. 9: time t1, indicated by a solid line), the corner part 21e of the first wire 21 in the inclined portion 201A is caught on an inner wall 92i and a distal blood vessel 922, and as a result, it is possible to increase the frictional resistance applied to the guide wire 1A as compared to a configuration without the inclined portion 201A (the lower part of FIG. 9). Consequently, in the proximal blood vessel 921, the distal end side of the guide wire 1A easily prolapses (curves) (the upper part of FIG. 9: time t2, indicated by a broken line).

In the prolapsing guide wire 1A, an orientation of the slope 21is of the inclined portion 201A and an orientation of the corner part 21e are each opposite to those described above. Therefore, when the prolapsing guide wire 1A is pushed into the distal blood vessel 922, it is possible to decrease the frictional resistance applied to the guide wire 1A as compared to the configuration without the inclined portion 201A, and it is therefore easy to push the guide wire 1A into the distal blood vessel 922. On the other hand, when the prolapsing guide wire 1A is pulled out of the distal blood vessel 922, it is possible to increase the frictional resistance applied to the distal end part of the guide wire 1A due to the presence of the corner parts 21e in the inclined portion 201A, and therefore, it is easy to cancel prolapse of the guide wire 1A (possible to bring the guide wire 1A back to a non-curved state).

Thus, the guide wire 1A according to the second embodiment may also exhibit an effect similar to that of the first embodiment. Specifically, the frictional resistances different between when the guide wire 1A is pushed forward and when the guide wire 1A is pulled back are applied, and thus, it is possible to improve the selectivity (vascular selectivity). It is also possible to facilitate the passage through the lesioned region and the constricted blood vessel in the flat portion 202. The inclined portion 201A is arranged at the distal end side and the flat portion 202 is arranged at the proximal end side, and thus, it is possible to prevent the guide wire 1A from damaging the inner wall 92i of a blood vessel 92, or the like. When the transverse sections of the first wire 21 and the second wire 22 forming the coil body 20A are of substantially elliptical shape, it is possible to prevent the corner part 21e from damaging the inner wall 92i of the blood vessel 92, or the like. In the guide wire 1A according to the second embodiment as well, similarly to the first embodiment, an outer diameter D2 at the distal end side of the coil body 20A and an outer diameter D21 at the proximal end side are substantially the same; however, the outer diameters D2 and D21 may be different from each other.

In the guide wire 1A according to the second embodiment, as compared to when the guide wire 1A passes through the healthy region in the blood vessel, the resistance obtained when the guide wire 1A is pushed forward after reaching the lesioned region increases, and thus, it is possible to improve the discriminability to determine whether the guide wire 1 reaches and passes through the lesioned region.

Third Embodiment

Figure 10:
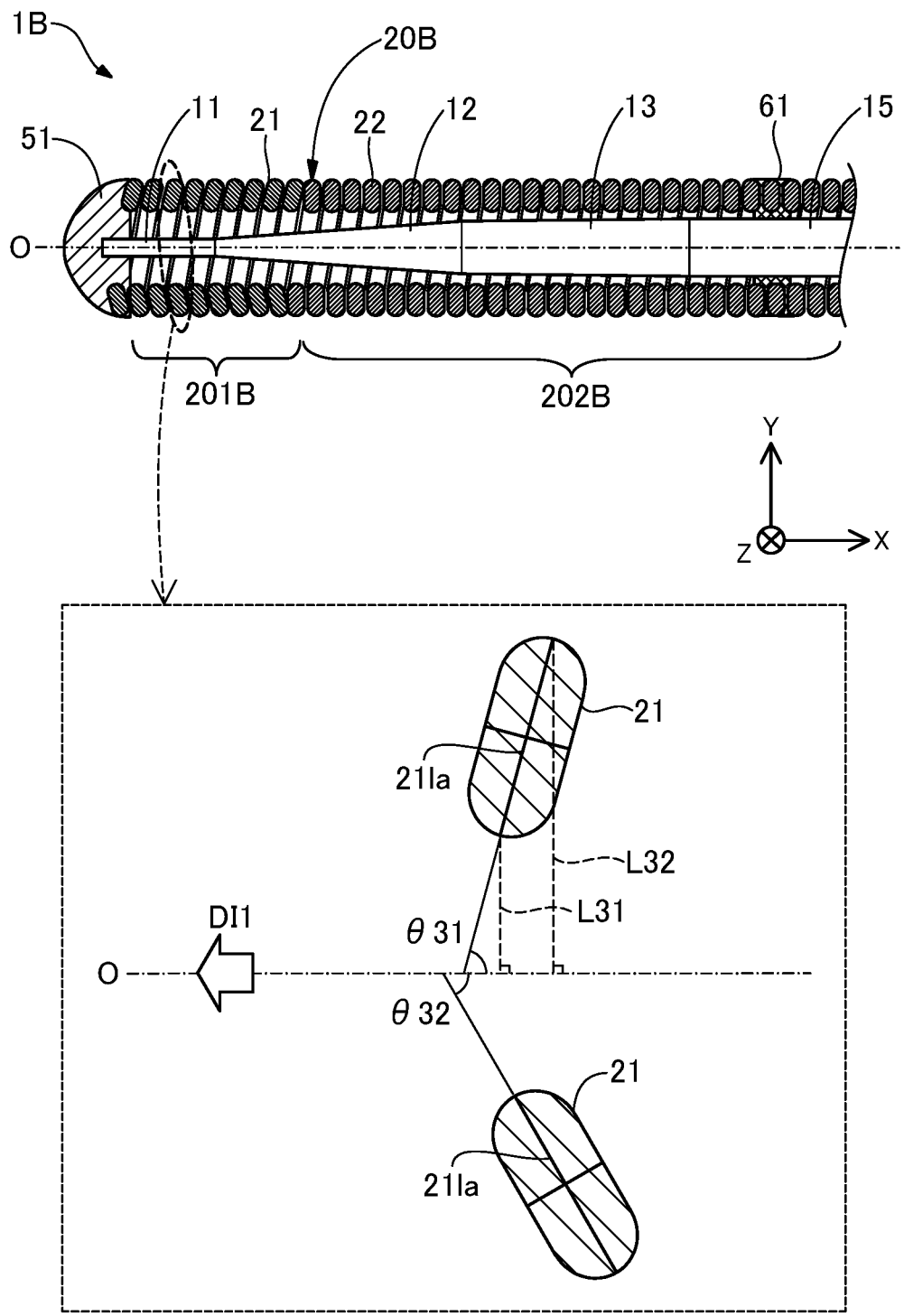
FIG. 10 is a partial sectional view of a distal end side of a guide wire according to a third embodiment.

FIG. 10 is a partial sectional view of a distal end side of a guide wire 1B according to a third embodiment. An upper part and a lower part of FIG. 10 are similar in configuration to those of FIG. 3. In a coil body 20B, the guide wire 1B according to the third embodiment includes an inclined portion 201B and a flat portion 202B in which the first wire 21 and the second wire 22 are wound at an angle different from that of the first embodiment.

As illustrated in the lower part of FIG. 10, in the first wire 21 in the inclined portion 201B, both angles θ31 and θ32 formed by the long axis 211a and the axial line O of the coil body 20B are larger than the angles θ11 and θ12 (FIG. 3) of the first embodiment, respectively. The angles θ31 and θ32 are both acute angles (that is, less than 90 degrees) with respect to the first direction DI1 along the axial line O. In the third embodiment, similarly to the first embodiment, the first direction DI1 is oriented toward the distal end side of the coil body 20B. The first wire 21 in the inclined portion 201B is oriented so that a distance L31 between an end point at the distal end side of the long axis 211a and the axial line O of the coil body 20B is shorter than a distance L32 between an end point at the proximal end side of the long axis 211a and the axial line O of the coil body 20B (that is, oriented toward the same direction as in the first embodiment).

As illustrated in the upper part of FIG. 10, in the second wire 22 in the flat portion 202B, the second wire 22 is rotated by about 90 degrees with respect to the second wire 22 of the first embodiment, and the long axis of the second wire 22 is perpendicular to the axial line O. Such a guide wire 1B according to the third embodiment exhibits an effect similar to that of the above-described first embodiment.

Fourth Embodiment

Figure 11:
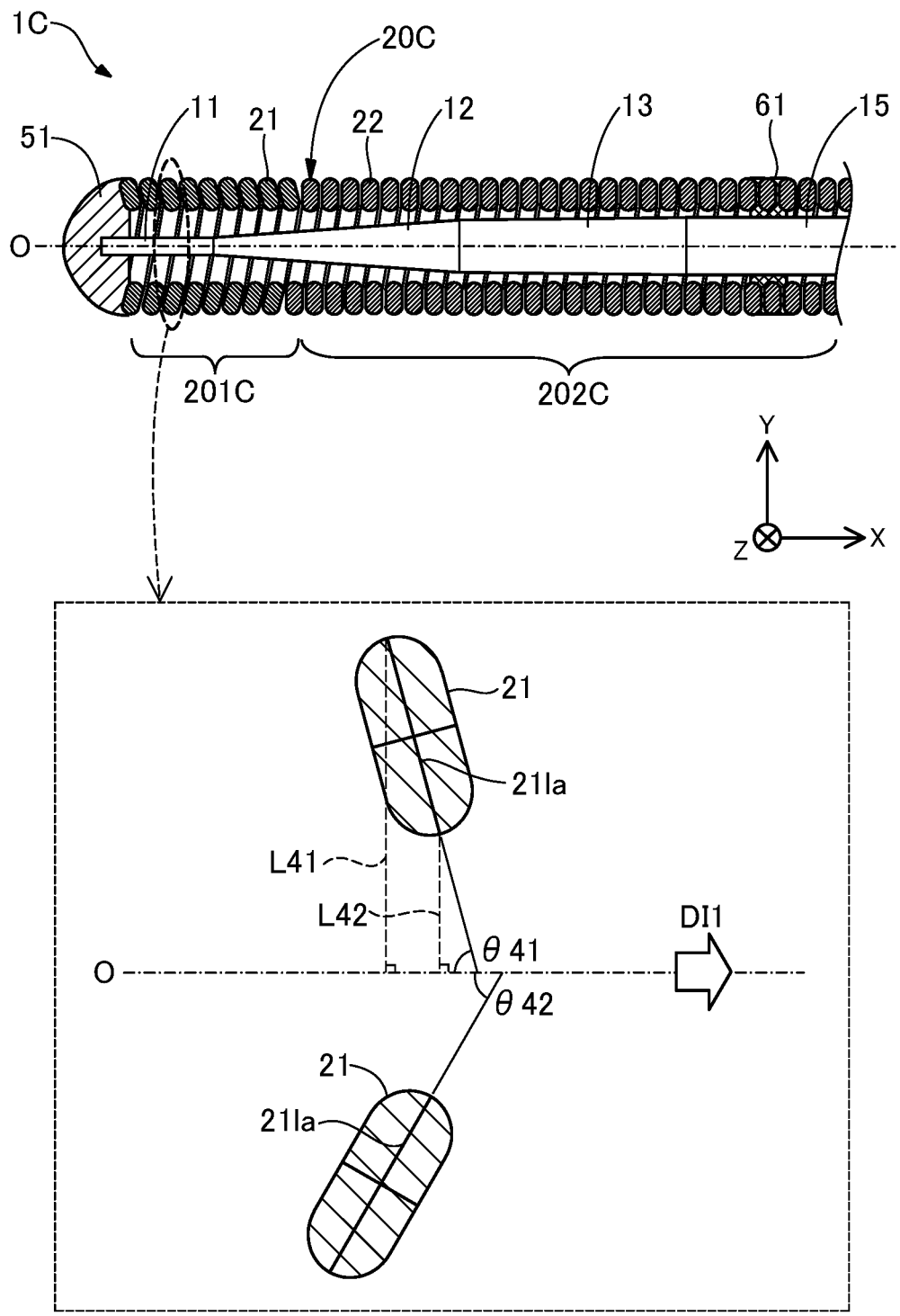
FIG. 11 is a partial sectional view of a distal end side of a guide wire according to a fourth embodiment.

FIG. 11 is a partial sectional view of a distal end side of a guide wire 1C according to a fourth embodiment. An upper part and a lower part of FIG. 11 are similar in configuration to those of FIG. 7. In a coil body 20C, the guide wire 1C according to the fourth embodiment includes an inclined portion 201C and a flat portion 202C in which the first wire 21 and the second wire 22 are wound at an angle different from that of the second embodiment.

As illustrated in the lower part of FIG. 11, in the first wire 21 in the inclined portion 201C, both angles θ41 and θ42 formed by the long axis 211a and the axial line O of the coil body 20C are larger than the angles θ21 and θ22 (FIG. 7) of the second embodiment, respectively. The angles θ41 and θ42 are both acute angles (that is, less than 90 degrees) with respect to the first direction DI1 along the axial line O. In the fourth embodiment, similarly to the second embodiment, the first direction DI1 is oriented toward the proximal end side of the coil body 20C. The first wire 21 in the inclined portion 201C is oriented so that a distance L41 between an end point at the distal end side of the long axis 211a and the axial line O of the coil body 20C is longer than a distance L42 between an end point at the proximal end side of the long axis 211a and the axial line O of the coil body 20C (that is, oriented toward the same direction as in the second embodiment).

As illustrated in the upper part of FIG. 11, in the second wire 22 in the flat portion 202C, the second wire 22 is rotated by about 90 degrees with respect to the second wire 22 of the second embodiment, and the long axis of the second wire 22 is perpendicular to the axial line O. Such a guide wire 1C according to the fourth embodiment exhibits an effect similar to that of the above-described second embodiment.

Fifth Embodiment

Figure 12:
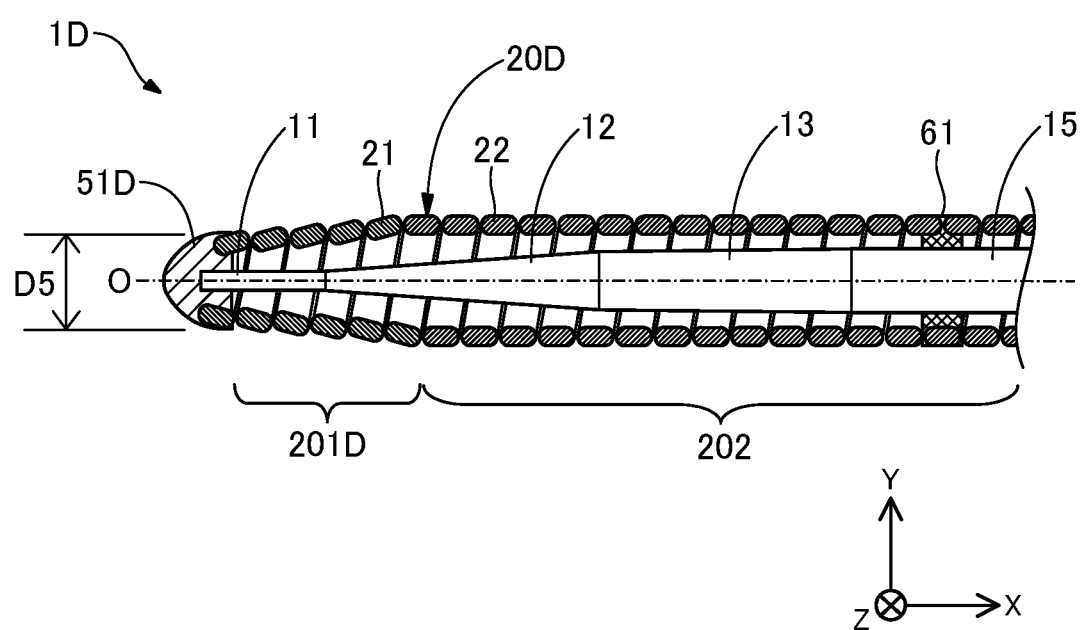
FIG. 12 is a partial sectional view of a distal end side of a guide wire according to a fifth embodiment.

FIG. 12 is a partial sectional view of a distal end side of a guide wire 1D according to a fifth embodiment. In the guide wire 1D according to the fifth embodiment, in an inclined portion 201D, the first wire 21 is wound so that a coil body 20D is gradually reduced in diameter from the proximal end side toward the distal end side. Therefore, in the guide wire 1D, the distance L12 (distance between the end point at the proximal end side of the long axis 211a of the first wire 21 and the axial line O of the coil body 20D) described in the first embodiment and the distance L11 (distance between the end point at the distal end side of the long axis 211a of the first wire 21 and the axial line O of the coil body 20) are both gradually reduced from the proximal end side toward the distal end side. That is, an outer diameter D5 at the distal end side of the coil body 20D is formed to be smaller than the outer diameter D11 (FIG. 1) at the proximal end side, and a distal end side fixing part 51D is also formed to be smaller in diameter than the distal end side fixing part 51 of the first embodiment.

Such a guide wire 1D according to the fifth embodiment exhibits an effect similar to that of the above-described first embodiment. The guide wire 1D according to the fifth embodiment has a thinner distal end part as compared to the guide wire 1 of the first embodiment, and thus, it is possible to further facilitate passage through a lesioned region.

Sixth Embodiment

Figure 13:
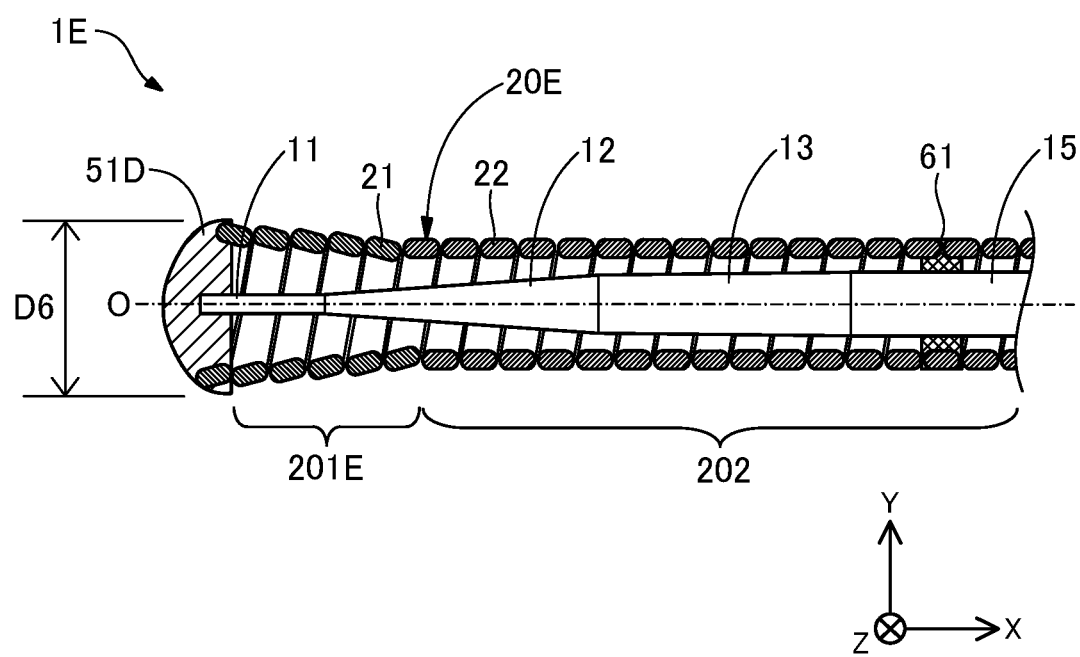
FIG. 13 is a partial sectional view of a distal end part of a guide wire according to a sixth embodiment.

FIG. 13 is a partial sectional view of a distal end part of a guide wire 1E according to a sixth embodiment. In the guide wire 1E according to the sixth embodiment, in an inclined portion 201E, the first wire 21 is wound so that a coil body 20E is gradually expanded in diameter from the proximal end side toward the distal end side. Therefore, in the guide wire 1E, the distance L22 (distance between the end point at the proximal end side of the long axis 211a of the first wire 21 and the axial line O of the coil body 20A) described in the second embodiment and the distance L21 (distance between the end point at the distal end side of the long axis 211a of the first wire 21 and the axial line O of the coil body 20A) are both gradually expanded from the proximal end side toward the distal end side. That is, an outer diameter D6 at the distal end side of the coil body 20E is formed to be larger than the outer diameter D21 (FIG. 6) at the proximal end side, and a distal end side fixing part 51E is also formed to be larger in diameter than the distal end side fixing part 51 of the second embodiment.

Such a guide wire 1E according to the sixth embodiment exhibits an effect similar to that of the above-described second embodiment. The guide wire 1E according to the sixth embodiment has a thicker distal end part as compared to the guide wire 1A according to the second embodiment, and thus, it is possible to further prevent the guide wire 1E from damaging the inner wall of a blood vessel, or the like.

Seventh Embodiment

Figure 14:
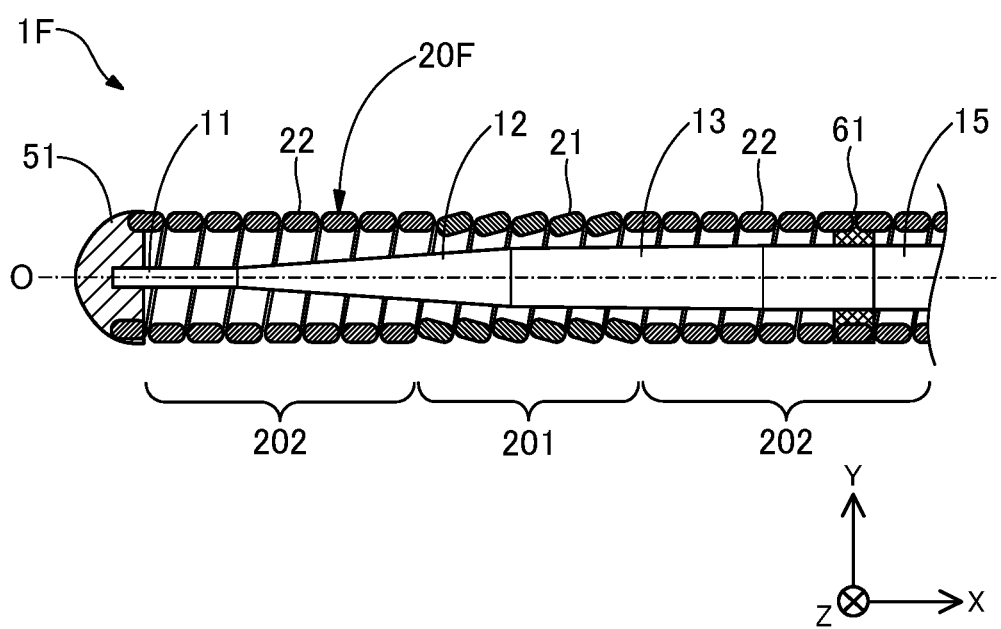
FIG. 14 is a partial sectional view of a distal end part of a guide wire according to a seventh embodiment.

FIG. 14 is a partial sectional view of a distal end part of a guide wire 1F according to a seventh embodiment. The guide wire 1F according to the seventh embodiment includes a coil body 20F in which parts, that is, the flat portion 202, the inclined portion 201, and the flat portion 202, are arranged in this order from the distal end side toward the proximal end side. Thus, the inclined portion 201 may not be arranged at the distal end side of the coil body 20F. For example, as illustrated, the flat portion 202 may be arranged at the distal end side of the coil body 20F. For example, the flat portion 202 may be arranged at the distal end side of the coil body 20F and the inclined portion 201 may be arranged at the proximal end side of the coil body 20F (that is, a configuration from which the flat portion 202 at the proximal end side is omitted in FIG. 14 may be employed). For example, a plurality of the inclined portions 201 and a plurality of the flat portions 202 may be provided, and the inclined portions 201 and the flat portions 202 may be arranged alternately along the axial line O direction. Such a guide wire 1F according to the seventh embodiment exhibits an effect similar to that of the above-described first embodiment.

Eighth Embodiment

Figure 15:
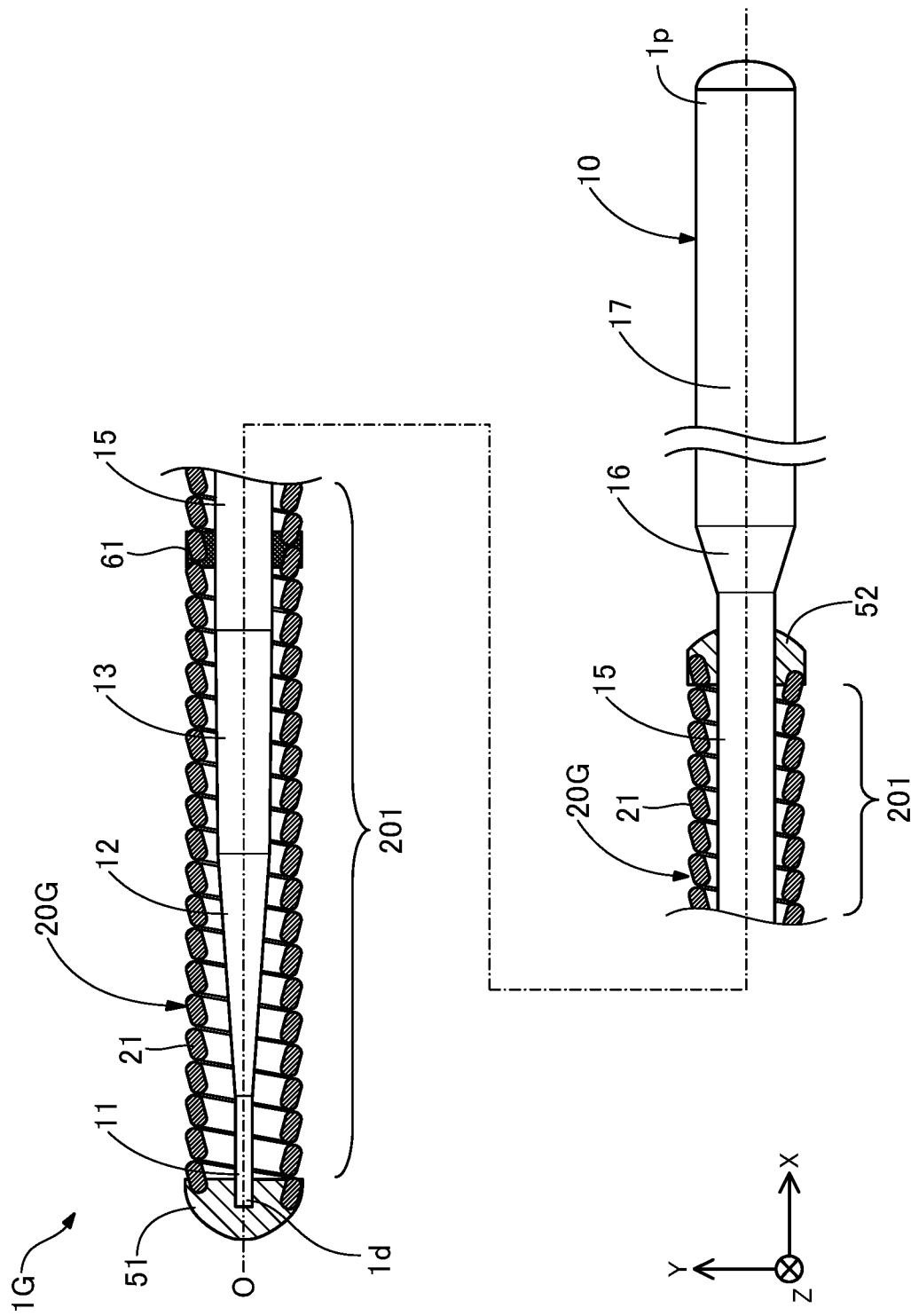
FIG. 15 is a partial sectional view illustrating an overall configuration of a guide wire according to an eighth embodiment.

FIG. 15 is a partial sectional view illustrating an overall configuration of a guide wire 1G according to an eighth embodiment. In the guide wire 1G, the flat portion 202 is omitted from the configuration of the guide wire 1 described in the first embodiment. That is, in the guide wire 1G, a coil body 20G is configured only by the inclined portion 201 and does not include the flat portion 202. Such a guide wire 1G according to the eighth embodiment exhibits an effect similar to that of the above-described first embodiment.

Ninth Embodiment

Figure 16:
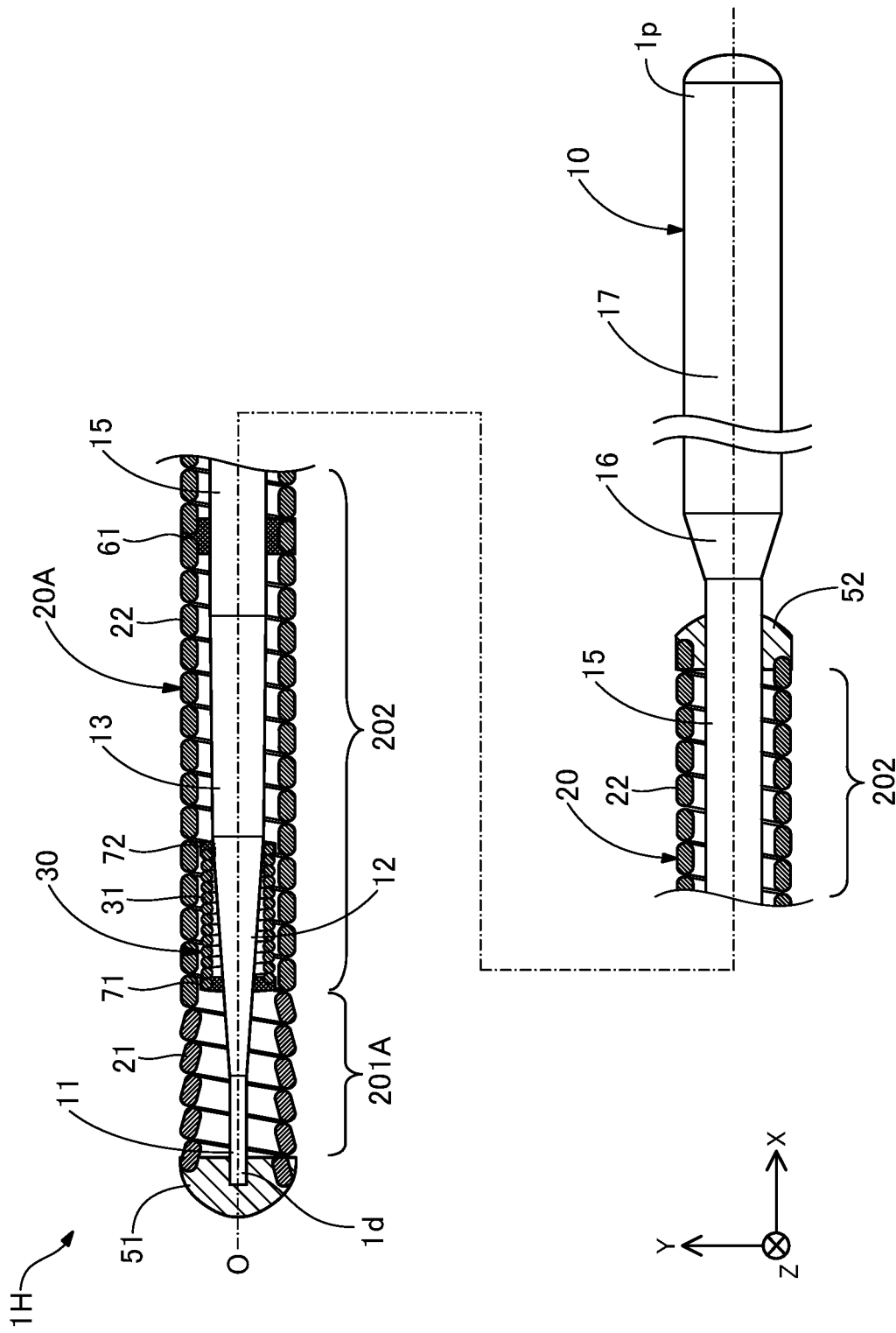
FIG. 16 is a partial sectional view illustrating an overall configuration of a guide wire according to a ninth embodiment.

FIG. 16 is a partial sectional view illustrating an overall configuration of a guide wire 1H according to a ninth embodiment. The guide wire 1H further includes an inner coil body 30 in addition to the components described in the guide wire 1A according to the second embodiment. The inner coil body 30 is formed by spirally winding a wire 31 around the core shaft 10 (first reduced-diameter part 12) inside the flat portion 202 of the coil body 20A. The wire 31 forming the inner coil body 30 may be a solid wire including a single wire or a strand obtained by twisting a plurality of wire. If the wire 31 is a solid wire, the inner coil body 30 is configured as a single coil, and if the wire 31 is a strand, the inner coil body 30 is configured as a hollow strand coil. The wire 31 may employ any material similarly to the second wire 22, for example. The wire 31 and the second wire 22 may employ the same material or employ different materials.

The inner coil body 30 is formed so that a length of the inner coil body 30 in the axial line O direction is shorter than that of the flat portion 202. The inner coil body 30 is arranged at the distal end side of the flat portion 202 in the axial line O direction. A distal end part of the inner coil body 30 is fixed to the core shaft 10 by an inner distal end fixing part 71, and a proximal end part thereof is fixed to the core shaft 10 by an inner proximal end fixing part 72. The inner distal end fixing part 71 and the inner proximal end fixing part 72 may be formed by any bonding agent, similarly to the distal end side fixing part 51. The inner distal end fixing part 71, the inner proximal end fixing part 72, and the distal end side fixing part 51 may employ the same bonding agent and different bonding agents.

Such a guide wire 1H according to the ninth embodiment exhibits an effect similar to that of the above-described second embodiment. The guide wire 1H according to the ninth embodiment includes the inner coil body 30 arranged at the distal end side of the flat portion 202. Therefore, when the guide wire 1H is used, if the distal end side of the guide wire 1H prolapses (curves), the guide wire 1H is supported by the inner coil body 30 so that it is possible to prevent the prolapse from progressing beyond the flat portion 202. As a result, in the guide wire 1H according to the ninth embodiment, it is possible to further improve operability.

Tenth Embodiment

Figure 17:
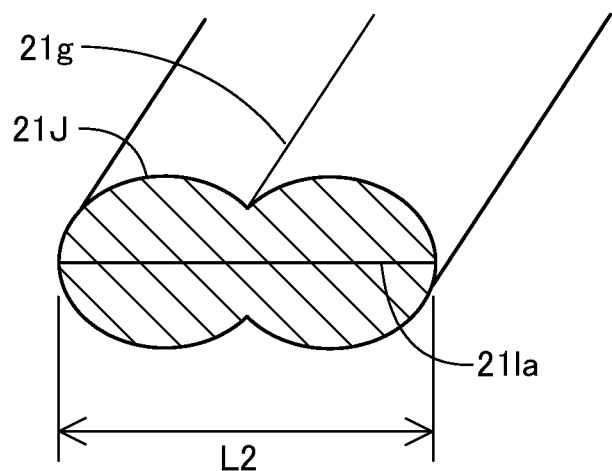
FIG. 17 is a transverse sectional view of a first wire according to a tenth embodiment.

FIG. 17 is a transverse sectional view of a first wire 21J according to a tenth embodiment. In the tenth embodiment, in the guide wire 1 described in the first embodiment, the inclined portion 201 is formed by using the first wire 21J instead of the first wire 21. As illustrated in FIG. 17, the first wire 21J has a shape in which two wires having transverse sections of substantially elliptical shape are connected to each other and includes a groove part 21g. A longest portion out of a length L2 in a longitudinal direction of the first wire 21J corresponds to the long axis 211a. It is possible to form the first wire 21J by, for example, passing a wire having a substantially rectangular transverse sectional shape through a die having a hole having a shape illustrated in FIG. 17.

Figure 18:
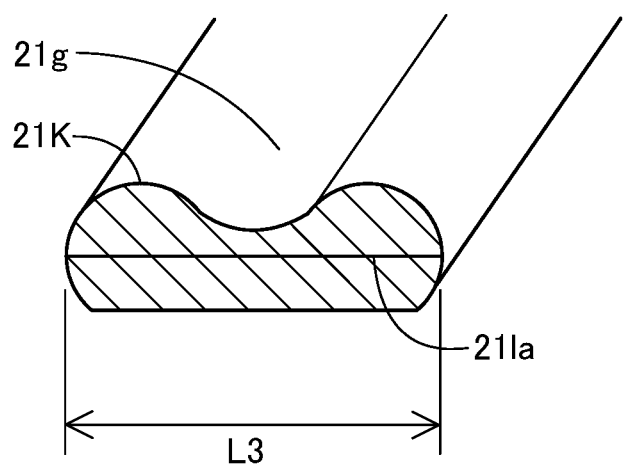
FIG. 18 is a transverse sectional view of the first wire according to the tenth embodiment.
Figure 19:
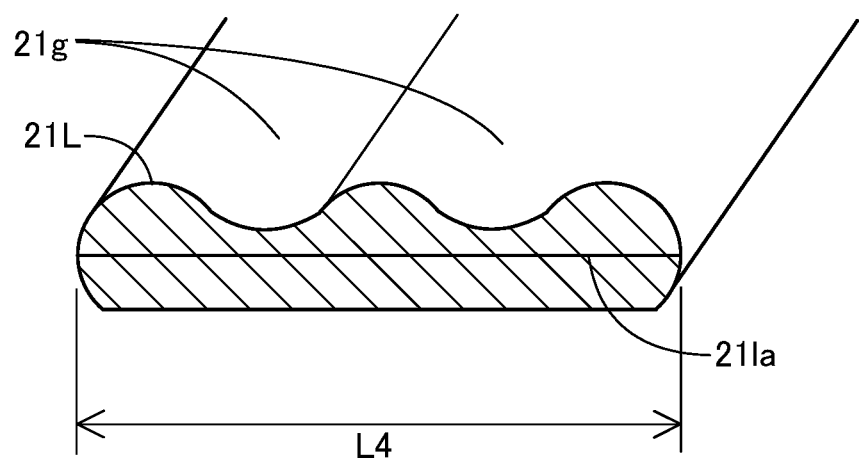
FIG. 19 is a transverse sectional view of the first wire according to the tenth embodiment.

FIG. 18 and FIG. 19 are transverse sectional views of first wires 21K and 21L according to the tenth embodiment. In the guide wire 1 described in the first embodiment, the inclined portion 201 may be formed by using the first wire 21K or the first wire 21L instead of the first wire 21. As illustrated in FIG. 18, the first wire 21K has a shape in which two wires having a substantially semicircular transverse section are connected to each other, and includes one groove part 21g. A longest portion out of a length L3 in a longitudinal direction of the first wire 21K corresponds to the long axis 211a. As illustrated in FIG. 19, the first wire 21L has a shape in which three wires having a substantially semicircular transverse section are connected to each other, and includes the two groove parts 21g. A longest portion out of a length L4 in a longitudinal direction of the first wire 21L corresponds to the long axis 211a.

The guide wire 1 in which such a first wire 21J, first wire 21K, or first wire 21L is used exhibits an effect similar to that of the above-described first embodiment. According to the guide wire 1 of the tenth embodiment, it is possible to enhance a frictional resistance of the inclined portion 201 because of the groove part 21g, and if the coil body 20 is coated with a resin layer, it is possible to prevent the resin layer from peeling.

Modification of Present Embodiment

Disclosed embodiments are not limited to the above-described embodiments, and may be implemented in various modes without departing from the spirit of the disclosed embodiments. The following modifications can be applied, for example.

First Modification

In the above-described first to tenth embodiments, examples of the configurations of the guide wires 1 and 1A to 1H are described. However, various modifications may be applied to the configurations of the guide wire. For example, the guide wire according to each of the above embodiments, which is described as a medical device used when a catheter is inserted into a blood vessel, may be configured to be inserted into various organs in a human body such as a lymphatic system, a biliary system, a urinary system, a respiratory system, a digestive system, a secretory gland, and reproductive organs. For example, the guide wire may be configured such that a whole of the core shaft is covered with the coil body without including the third reduced-diameter part 16 and the second large-diameter part 17.

Second Modification

In the above-described first to tenth embodiments, the examples of the configurations of the core shaft 10 are provided. However, various modifications may be applied to the configurations of the core shaft. For example, the configurations of the core shaft may be in which the core shaft includes a first core shaft arranged at the proximal end side and a second core shaft (may be referred to as "ribbon") arranged at the distal end side, and the first core shaft and the second core shaft are joined.

Third Modification

In the above-described first to tenth embodiments, examples of the configurations of the coil bodies 20 and 20A to 20G are provided. However, various modifications may be applied to the configurations of the coil body. For example, the flat portion of the coil body may be formed by using a wire having a substantially circular transverse section (wire not including the long axis and the short axis). For example, the inclined portion and the flat portion may be formed by using the same wire (wires formed of the same material and having the same shape).

For example, the inclined portion of the coil body may be configured to be in a loosely wound manner where there is a gap between the adjacent first wires. Similarly, the flat portion of the coil body may be configured to be in a loosely wound manner where there is a gap between the adjacent second wires. The coil body may include, for example, a resin layer coated with a hydrophobic resin material, a hydrophilic resin material, or a mixture thereof. The resin layer may be arranged to cover only the inclined portion or only the flat portion, and may be arranged to cover an area near a boundary portion between the inclined portion and the flat portion (for example, a joint portion between the first wire and the second wire). The resin layer may be arranged to cover the entire coil body (both the inclined portion and the flat portion).

Fourth Modification

The configurations of the guide wires 1 and 1A to 1H according to the first to tenth embodiments and the configurations of the guide wires of the first to third modifications may be appropriately combined. For example, in the guide wire 1 (FIG. 1) according to the first embodiment, the configuration in which the diameter at the distal end side is expanded described in the sixth embodiment may be adopted, and the configuration including the inner coil body described in the ninth embodiment may be adopted. For example, in the guide wire 1A (FIG. 6) according to the second embodiment, the configuration in which the diameter at the distal end side described in the fifth embodiment is reduced may be adopted, and the arrangement of the inclined portion and the flat portion described in the seventh embodiment may be adopted. For example, in the guide wires according to the second to ninth embodiments, the wire having the shape described in the tenth embodiment may be used to form at least one of the inclined portion and the flat portion.

Although the aspects have been described based on the embodiments and the modifications, the embodiments of the above-described aspects are for facilitating understanding of the aspects, and does not limit the aspects. The aspects can be modified and improved without departing from the spirit and scope of the claims, and its equivalents are included in the aspects. Further, unless the technical features are described as essential in the present specification, it may be omitted as appropriate.

DESCRIPTION OF REFERENCE NUMERALS 1, 1A to 1H . . . Guide wire
10 . . . Core shaft
11 . . . Small-diameter part
12 . . . First reduced-diameter part
13 . . . Second reduced-diameter part
15 . . . First large-diameter part
16 . . . Third reduced-diameter part
17 . . . Second large-diameter part
20, 20A to 20G . . . Coil body
21, 21J to 21L . . . First wire
21e . . . Corner part
21g . . . Groove part
21is . . . Slope
211a . . . Long axis
21ma . . . Short axis
22 . . . Second wire
23 . . . Joint part
30 . . . Inner coil body
31 . . . Wire
51, 51D, 51E . . . Distal end side fixing part
52 . . . Proximal end side fixing part
61 . . . Intermediate fixing part
71 . . . Inner distal end fixing part
72 . . . Inner proximal end fixing part

What is claimed is:
1. A guide wire comprising:
a core shaft; and
a coil body including a wire wound around the core shaft, wherein
the wire includes a long axis and a short axis in a transverse section,
the coil body includes an inclined portion where angles formed by the long axis of the wire and an axial line of the coil body are acute on both sides of the axial line in a longitudinal section along the axial line, the angles being on a proximal side of an intersection between the axial line and the long axis, and
the guide wire further comprises a fixing part positioned at a distal end of the guide wire and configured to integrally hold a distal end of the core shaft and a distal end of the inclined portion.
2. The guide wire according to claim 1, wherein
the coil body further includes a flat portion in which the long axis of the wire and the axial line of the coil body are parallel to each other.
3. The guide wire according to claim 2, wherein
the inclined portion is arranged at a distal end side of the coil body, and
the flat portion is arranged at a proximal end side of the coil body.
4. The guide wire according to claim 3, wherein
in the inclined portion, the wire is positioned so that a distance between an end point of the wire at a distal end side of the wire on the long axis and the axial line is shorter than a distance between an end point of the wire at a proximal end side of the wire on the long axis and the axial line.

5. The guide wire according to claim 3, wherein in the inclined portion, the wire is positioned such that a distance between an end point of the wire at a distal end side of the wire on the long axis and the axial line is longer than a distance between an end point of the wire at a proximal end side of the wire on the long axis and the axial line.

6. The guide wire according to claim 3, wherein a transverse section of the wire is of substantially elliptical shape.

7. The guide wire according to claim 3, wherein the flat portion is further arranged at a central portion of the coil body.

8. The guide wire according to claim 2, wherein in the inclined portion, the wire is positioned so that a distance between an end point of the wire at a distal end side of the wire on the long axis and the axial line is shorter than a distance between an end point of the wire at a proximal end side of the wire on the long axis and the axial line.

9. The guide wire according to claim 2, wherein in the inclined portion, the wire is positioned such that a distance between an end point of the wire at a distal end side of the wire on the long axis and the axial line is longer than a distance between an end point of the wire at a proximal end side of the wire on the long axis and the axial line.

10. The guide wire according to claim 2, wherein a transverse section of the wire is of substantially elliptical shape.

11. The guide wire according to claim 2, wherein the flat portion extends for a greater length of the coil body than the inclined portion.

12. The guide wire according to claim 1, wherein in the inclined portion, the wire is positioned so that a distance between an end point of the wire at a distal end side of the wire on the long axis and the axial line is shorter than a distance between an end point of the wire at a proximal end side of the wire on the long axis and the axial line.

13. The guide wire according to claim 12, wherein a transverse section of the wire is of substantially elliptical shape.

14. The guide wire according to claim 1, wherein in the inclined portion, the wire is positioned such that a distance between an end point of the wire at a distal end side of the wire on the long axis and the axial line is longer than a distance between an end point of the wire at a proximal end side of the wire on the long axis and the axial line.

15. The guide wire according to claim 14, wherein a transverse section of the wire is of substantially elliptical shape.

16. The guide wire according to claim 1, wherein a transverse section of the wire is of substantially elliptical shape.

17. The guide wire according to claim 1, wherein in the inclined portion, the wire has a plurality of inclined surfaces which are inclined relative to the axial line of the coil body.

* * * * *